United States Patent [19]
Arbir et al.

[11] 4,307,109
[45] Dec. 22, 1981

[54] BIOCIDAL CHELATE

[75] Inventors: Francis W. Arbir, Itasca; William J. Rizoff, Waukegan; Frank C. Becker, Gurnee, all of Ill.

[73] Assignee: Abbott Laboratories, North Chicago, Ill.

[21] Appl. No.: 147,767

[22] Filed: May 8, 1980

[51] Int. Cl.$^3$ .................. A01N 43/36; A61K 31/40
[52] U.S. Cl. ................... 424/274; 424/319; 424/DIG. 6
[58] Field of Search ............... 424/DIG. 6, 274, 319

[56] References Cited

U.S. PATENT DOCUMENTS

| 2,474,412 | 6/1949 | Bersworth | 252/106 |
| 2,524,219 | 10/1950 | Bersworth | 260/482 |
| 2,624,756 | 1/1953 | Bersworth | 260/518 |
| 4,141,905 | 2/1979 | Becker et al. | 424/274 X |

OTHER PUBLICATIONS

Chemical Abstracts 85:733w (1976).

*Primary Examiner*—Leonard Schenkman
*Attorney, Agent, or Firm*—Robert L. Niblack; Paul D. Burgauer

[57] ABSTRACT

The biocidal activity of N-(2-methyl-1-naphthyl)-maleimide is vastly improved by chelating it with an amine wherein each free hydrogen on each amino group has been replaced by the groups —(CH$_2$)$_n$COOY wherein n represents 1 or 2 and each Y represents hydrogen, ammonium or an alkali metal cation.

10 Claims, No Drawings

BIOCIDAL CHELATE

DETAILED DESCRIPTION OF THE INVENTION

From U.S. Pat. No. 4,141,905 it is known that N-(2-methyl-1-naphthyl)-maleimide is a fine biocide for use in paints, on textiles and in plastics. Unfortunately, N-(2-methyl-1-naphthyl)-maleimide is not an inexpensive material and if effective biocidal activity is to be achieved and maintained on any substrate, amounts of 50–50,000 ppm have to be used.

It has now been found that a surprisingly high synergism exists when N-(2-methyl-1-naphthyl)-maleimide is combined with chelates. The present invention is therefore directed to the process of protecting a substrate by coating it or incorporating into it a biocidally active amount of a combination between N-(2-methyl-1-naphthyl)-maleimide and a chelator. This combination may contain equal parts of the two components or the ratio between N-(2-methyl-1-naphthyl)-maleimide and the chelator may be 1:150.

The preferred chelators to be used in the present invention are the polyacetate or polypropionate (poly)amines in the acid form or as fully or partially neutralized alkali or ammonium salts, e.g., diethylenetriamine penta-acetic acid, ethylenediamine tetraacetic acid, the sodium or ammonium salt of these two compounds, tetrasodium or triammonium ethylenediamine tetra-acetic acid, its potassium salts, and the like. These chelators have extremely low biocidal activity by themselves and it is therefore unexpected that they greatly enhance or potentiate the activity of N-(2-methyl-1-naphthyl)-maleimide, even when used in a small fraction of the amount that would have some biocidal activity alone, and when using amounts of 7.5–65% of the minimum amount of N-(2-methyl-1-naphthyl)-maleimide contemplated by U.S. Pat. No. 4,141,905.

The current synergistic biocide is particularly useful for the treatment of leather, leather substitutes, wood, plastic products, or fabrics made from cellulosic or olefine polymers, knitted, woven, extruded or molded into structures exposed to outdoor conditions, such as outdoor-wear, tents, boots, belts, saddles, tarpaulins, swimming pool liners, swim-wear and the like. The new chelate can also be employed as an additive to industrial fluids, e.g., cooling water, hydrocarbon fluids, metal cutting fluid; it can also be incorporated for its biocidal effect into cosmetics and, of course, paints of all types, including alkyd, oil-based or latex paints.

When the substrate is treated with the chelate of this invention, growth of bacteria and fungi is also inhibited in areas in contact with the treated areas. Treated areas are to be understood as those in which the new chelate has been incorporated as a manufacturing ingredient, i.e., a biocidally active proportion has been added to the polymer mixture before it was shaped by molding or extruding it into the ultimate form, or it has been added to the surface of such a substrate or any other material, including wood, plasterboard, textiles from natural or snythetic filters by surface coating, dipping, spraying, etc., or is added to cosmetics such as lipstick, shampoo, face cream and powder or to surgical soaps or disinfectants.

In order to illustrate the effect of the new chelate, reference is made to the following example which, however, is not intended to limit the invention in any respect. In this example, minimum inhibitory concentrations (MIC) were determined by using standard microtiter techniques and making serial dilutions of the various compounds. The tests were conducted using a mixture of A. aerogenes and Pseudomona as the microorganisms.

The table below reproduces the results obtained by this microtiter dilution method, with the codes A–G having the following meaning:
A. N-(2-methyl-1-naphthyl)-maleimide
B. Diethylenetriamine pentacetic acid
C. Ethylenediamine tetraacetic acid
D. Diammonium ethylenediamine tetraacetic acid
E. Tetrasodium ethylenediamine tetraacetic acid
F. Trisodium ethylenediamine tetraacetic acid
G. Liquid chelator mixture sold as Hampene Fe-62 (a balanced liquid blend of chelating agents especially designed to complex iron in alkaline solutions, marketed by W. R. Grace & Co.).

| Compound | 24 hrs. | 48 hrs. | 84 hrs. | 96 hrs. |
|---|---|---|---|---|
| A | 62.5 | 62.5 | 125 | 125 |
| B | 2000 | 2000 | 500 | 1000 |
| C | 2000 | 2000 | 1000 | 2000 |
| D | 4000 | >4000 | 4000 | 4000 |
| E | >4000 | >4000 | 2000 | 2000 |
| F | >4000 | >4000 | 4000 | 4000 |
| G | >4000 | >4000 | 4000 | 4000 |
| A/B | 3.9/125 | 3.9/500 | 3.9/500 | 3.9/500 |
| | 7.8/62.5 | 7.8/250 | 7.8/500 | 7.8/500 |
| | 15.6/31.2 | 15.6/62.5 | 15.6/250 | 15.6/250 |
| | 31.2/31.2 | 31.2/31.2 | 31.2/125 | 31.2/125 |
| A/C | 3.9/500 | 3.9/1000 | 3.9/1000 | 3.9/1000 |
| | 7.8/250 | 7.8/500 | 7.8/1000 | 7.8/1000 |
| | 15.6/125 | 15.6/250 | 15.6/500 | 15.6/500 |
| | 31.2/62.5 | 31.2/125 | 31.2/500 | 31.2/500 |
| A/D | 3.9/500 | 3.9/1000 | 3.9/1000 | 3.9/1000 |
| | 7.8/250 | 7.8/1000 | 7.8/1000 | 7.8/1000 |
| | 15.6/125 | 15.6/500 | 15.6/1000 | 15.6/1000 |
| | 31.2/31.2 | 31.2/125 | 31.2/1000 | 31.2/1000 |
| A/E | 3.9/500 | Growth at 3.9 | Growth at 3.9 | Growth at 3.9 |
| | 7.8/500 | Growth at 7.8 | Growth at 7.8 | Growth at 7.8 |
| | 15.6/250 | 15.6/1000 | 15.6/1000 | 15.6/1000 |
| | 31.2/62.5 | 31.2/250 | 31.2/1000 | 31.2/1000 |
| A/F | 3.9/1000 | Growth at 3.9 | Growth at 3.9 | Growth at 3.9 |
| | 7.8/500 | 7.8/1000 | Growth at 7.8 | Growth at 7.8 |
| | 15.6/250 | 15.6/500 | 15.6/1000 | 15.6/1000 |
| | 31.2/62.5 | 31.2/250 | 31.2/500 | 31.2/250 |
| A/G | 3.9/1000 | Growth at 3.9 | Growth at 3.9 | Growth at 3.9 |
| | 7.8/500 | Growth at 7.8 | Growth at 7.8 | Growth at 7.8 |
| | 15.6/500 | 15.6/1000 | 15.6/2000 | 15.6/2000 |
| | 31.2/62.5 | 31.2/500 | 31.2/1000 | 31.2/1000 |

All parts are shown as parts per million.

From the above, it is apparent that an unusual level of synergism is obtained by the new chelate combination. With chelating agents having a MIC of 2000 to >4000 ppm, their level can be reduced to 1/16 to ¼ for a 96 hour protection level. Similarly striking is the reduction of N-(2-methyl-1-naphthyl)-maleimide: where this compound alone requires 125 ppm for 96 hour protection, only 1/16–¼ of that amount is needed when combined with any of the chelators. A biocidally effective combination, as seen from the above table, consists of a mixture of N-(2-methyl-1-naphthyl)-maleimide and a chelator in a weight ratio of about 1:100 to 1:1, preferably 1:10 to 1:4. The amount of such a mixture is then determined depending on the length of protection required, the severity of the exposure to micro-organisms or the climatic environment. In any case, the amount of either component in the mixture need only be ¼ or less than the amount of either component alone to afford similar protection.

The new mixture of components can easily be prepared by just milling the two materials together in the desired ratio, until homogeneity is obtained. Under normal storage conditions, this mixture is stable for essentially indefinite periods of time, although it should be observed that extended exposure to heat and moisture might be damaging to it.

Even though the above tests were performed with bacteria only, similar potentiation of N-(2-methyl-1-naphthyl)-maleimide is seen when the new chelates are used against fungi, yeasts, spores and other micro-organisms. Again, in U.S. Pat. No. 4,141,905, N-(2-methyl-1-naphthyl)-maleimide has shown to have broad biocidal activity alone, and that activity is enhanced with the chelates, whether the chelates are based on acetic acid (salts) or propionic acid (salts).

It will be apparent that the term "substrate" used above is to be understood in its broadest term. Substrates can be coated with the above chelates per se or a paint or pigment mixture containing such chelates. In the case of paint, the chelate can be added thereto by the manufacturer due to the compatibility thereof with all types of paints, or it can be added at the time of use. In outdoor use structures or fabrics, the new chelates can be sprayed on, or a fabric can be soaked in a liquid containing the chelate, or in the case of synthetic fabrics, the new chelates can be added to the mixture from which such synthetics are made. Also, similar to the use with paints, fibers often used in outdoor furniture or fabrics can be dyed in a bath containing the above chelates.

The new chelates are also effective in combatting micro-organisms in industrial fluids, i.e., cutting and other metal-working fluids, as a wood preservative through vacuum impregnation or by surface application, as protection in rain gear including umbrella fabrics, tarpaulins, raincoats, plastic hair covers, and the like. The substrates can thus be cellulose-based, synthetic materials, textiles, woods, plastics, polymers, leather, paints, etc. In all instances, the new chelates prevent the growth of the most common micro-organisms.

We claim:

1. The method of protecting a substrate against bacterial and fungal attack upon exposure to an environment containing common fungi or bacteria, comprising incorporating into said substrate or surface-coating said substrate with a biocidally effective amount of a chelate, said chelate comprising 1 part of N-(2-methyl-1-naphthyl)-maleimide and 1–100 parts by weight of ethylenediamine or diethylenetriamine wherein each free hydrogen on each amino group has been replaced by the moiety $-(CH_2)_n COOY$ wherein n is 1 or 2 and Y is hydrogen, ammonium or an alkali metal cation.

2. The method of claim 1 wherein said amine is present at a ratio of between 4 and 10 weight parts per part of N-(2-methyl-1-naphthyl)-maleimide.

3. The method of claim 1 wherein said amine is diethylenetriamine pentaacetic acid.

4. The method of claim 1 wherein said amine is ethylenediamine tetraacetic acid.

5. The method of claim 1 wherein said amine is tetrasodium ethylenediamine tetraacetic acid.

6. A biocide for use in preventing the growth of micro-organisms, comprising one part by weight of N-(2-methyl-1-naphthyl)-maleimide and between 1 and 100 parts by weight of ethylenediamine or diethylenetriamine wherein each free hydrogen on each amino group has been replaced by the moiety $-(CH_2)_n COOY$ wherein n is 1 or 2 and Y is hydrogen, ammonium or an alkali metal cation.

7. A biocide according to claim 6 wherein said amine is present in an amount of 4–10 parts by weight.

8. The biocide of claim 7 wherein said amine is diethylenetriamine pentaacetic acid.

9. The biocide of claim 7 wherein said amine is ethylenediamine tetraacetic acid.

10. The biocide of claim 7 wherein said amine is tetrasodium ethylenediamine tetraacetic acid.

* * * * *